United States Patent [19]
Okazaki et al.

[11] Patent Number: 5,524,625
[45] Date of Patent: Jun. 11, 1996

[54] SHOCK WAVE GENERATING SYSTEM CAPABLE OF FORMING WIDE CONCRETION-DISINTEGRATING REGION BY ENERGIZING RING-SHAPED TRANSDUCERS, AND HYPERTHERMIA CURING SYSTEM

[75] Inventors: Kiyoshi Okazaki; Yuji Yanagida; Nobuyuki Iwama, all of Tochigiken, Japan

[73] Assignee: Kabushiki Kaisha Toshiba, Kawasaki, Japan

[21] Appl. No.: 322,359

[22] Filed: Oct. 13, 1994

Related U.S. Application Data

[63] Continuation of Ser. No. 29,659, Mar. 10, 1993, abandoned.

[30] Foreign Application Priority Data

Mar. 10, 1992 [JP] Japan .................... 4-051634
Jun. 15, 1992 [JP] Japan .................... 4-154920

[51] Int. Cl.⁶ .................................................. A61B 17/22
[52] U.S. Cl. .................... 128/660.03; 601/3; 601/4; 607/97
[58] Field of Search .................. 128/660.03; 601/2–4; 607/97

[56] References Cited

U.S. PATENT DOCUMENTS

| 4,955,366 | 9/1990 | Uchiyama et al. | 128/24 EL |
| 5,062,412 | 11/1991 | Okazaki | 128/24 |
| 5,103,805 | 4/1992 | Okazaki | 128/24 EL |
| 5,203,333 | 4/1993 | Nomura | 601/4 |
| 5,207,214 | 5/1993 | Romano | 128/24 EL |

*Primary Examiner*—Ruth S. Smith
*Attorney, Agent, or Firm*—Foley & Lardner

[57] ABSTRACT

In a shock wave generating system, a width of a focused region synthesized from a plurality of focal points formed by a plurality of shock waves is varied by properly controlling delay times and/or drive voltages for a plurality of ring-shaped piezoelectric transducer elements. The shock wave generating system includes a shock wave generating unit having a plurality of shock-wave generating elements and a driving unit for separately driving the plurality of shock-wave generating elements by controlling at least delay times to produce a plurality of shock waves in such a manner that a dimension of a focused region synthesized from a plurality of different focal points formed by the plurality of shock waves, is varied in accordance with a dimension of a concretion to be disintegrated which is present in a biological body under medical examination.

13 Claims, 15 Drawing Sheets

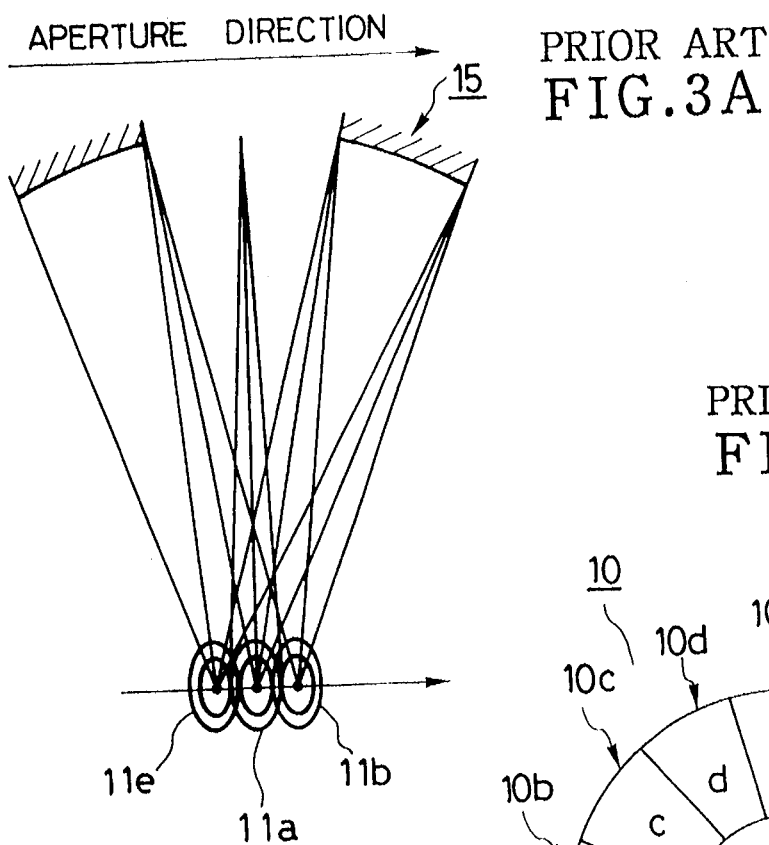
PRIOR ART
FIG. 3A
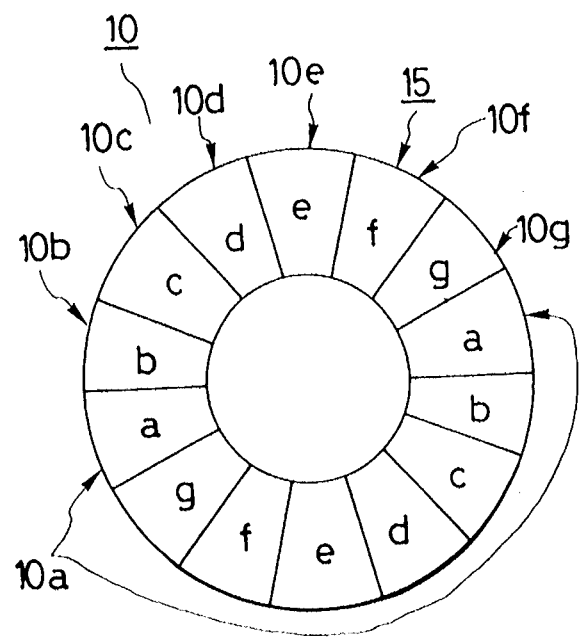
PRIOR ART
FIG. 3B
PRIOR ART
FIG. 3C
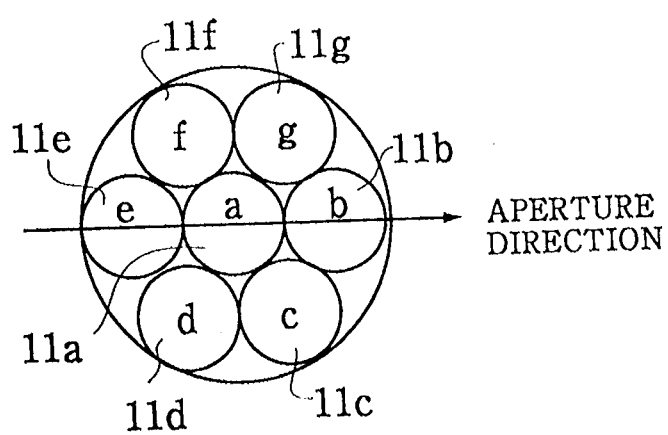

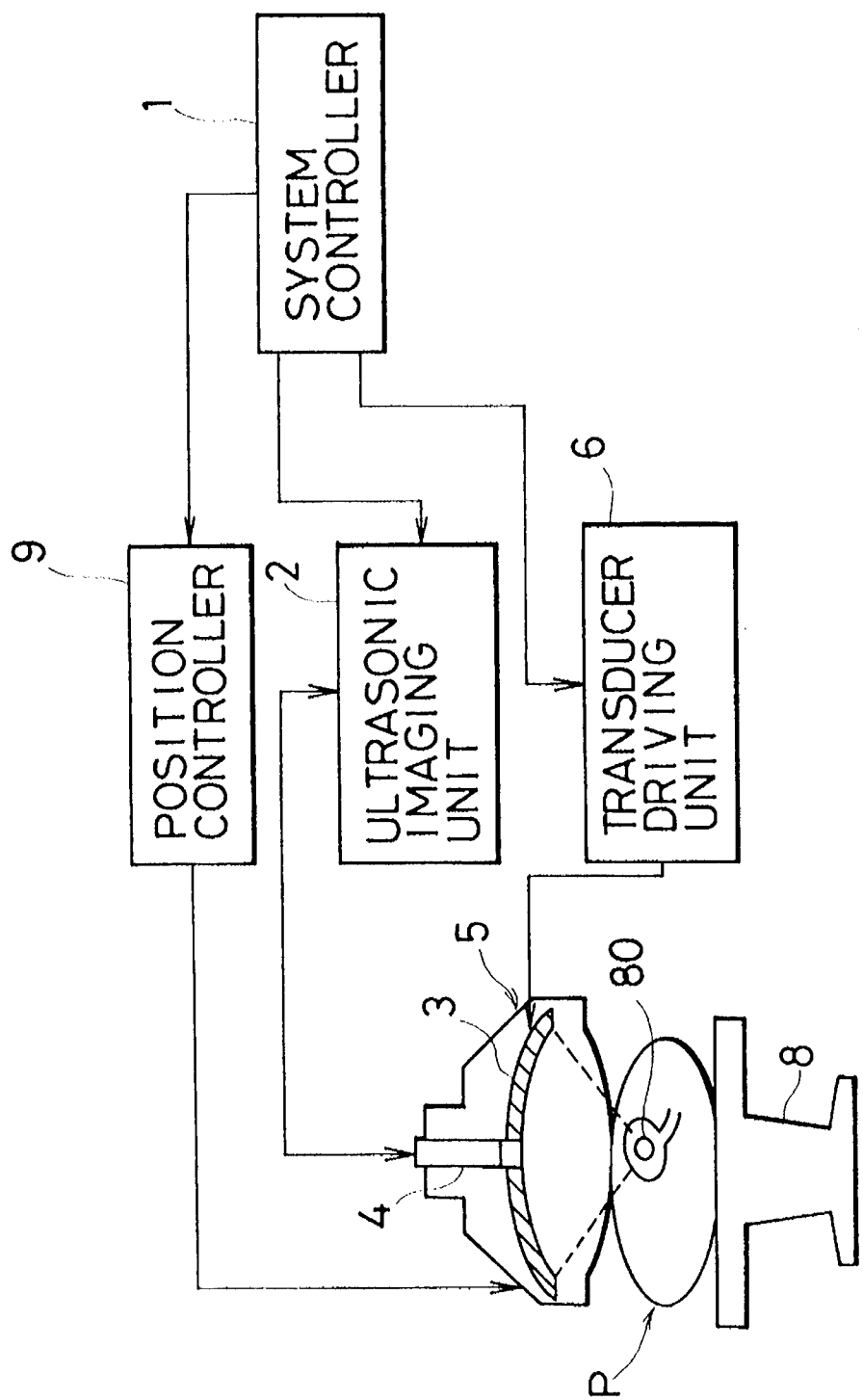

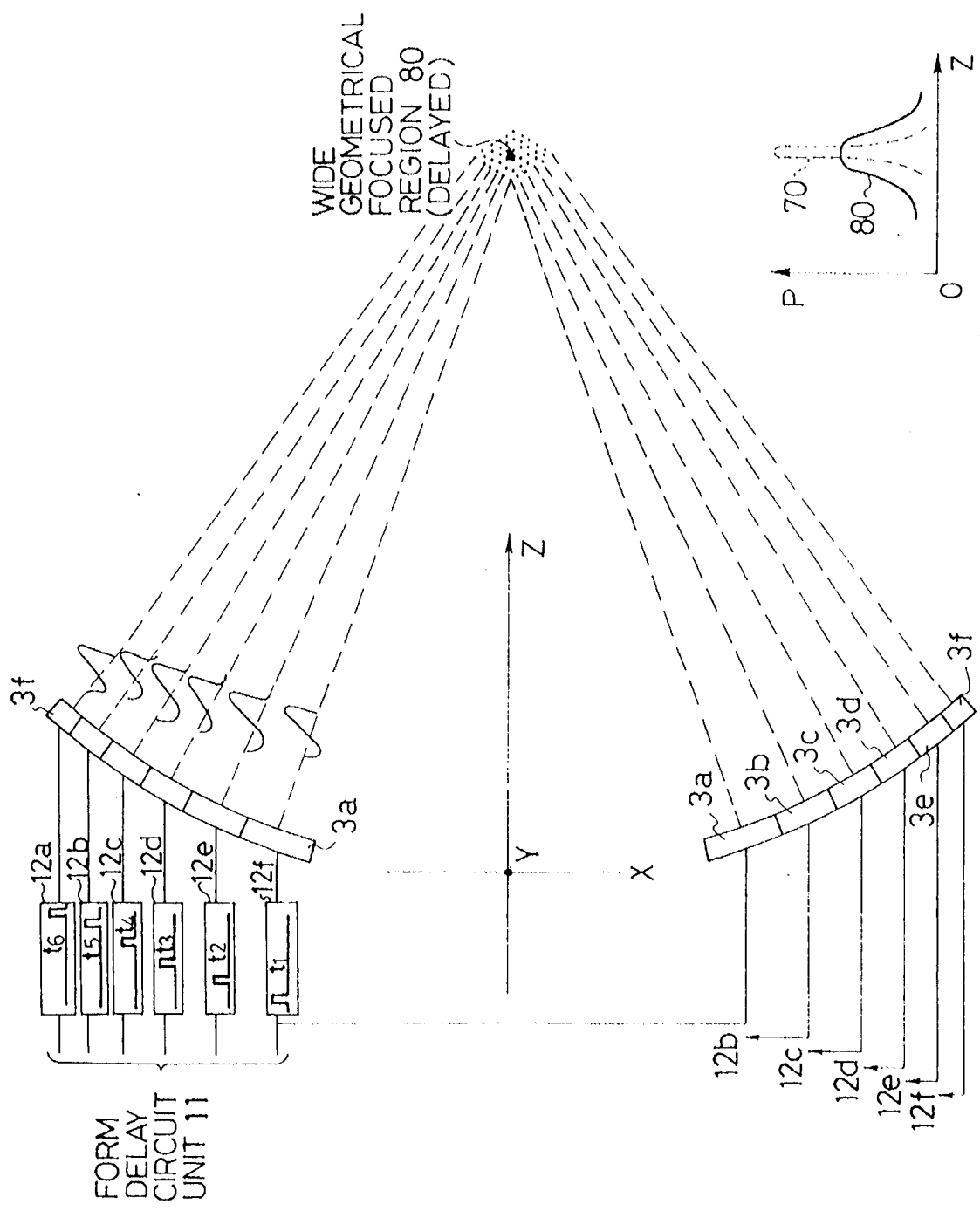

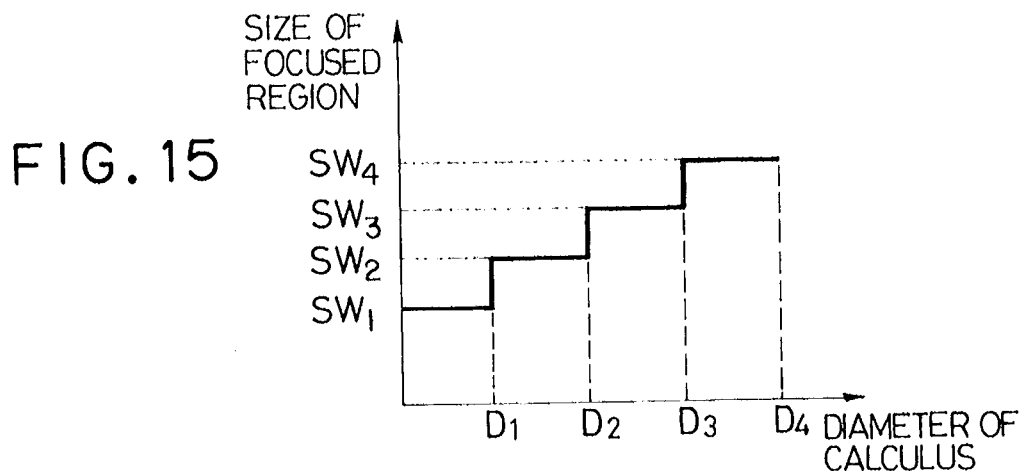
FIG. 15
FIG. 16A
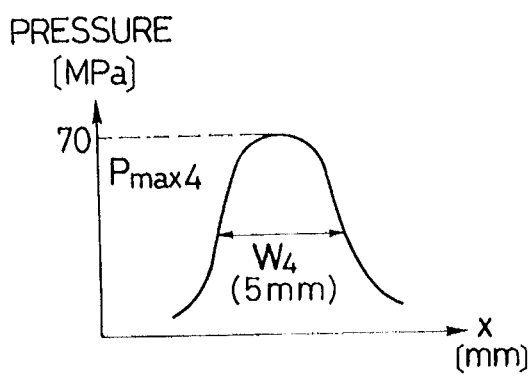
FIG. 17A
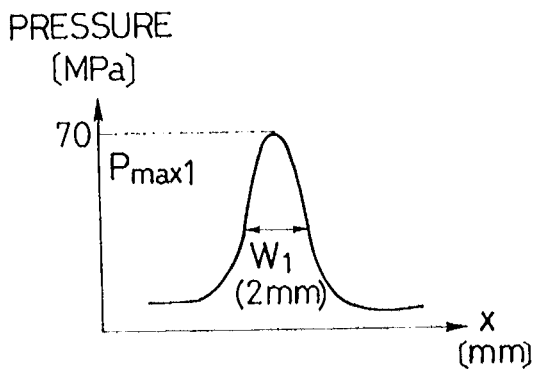
FIG. 16B
FIG. 17B

SHOCK WAVE GENERATING SYSTEM CAPABLE OF FORMING WIDE CONCRETION-DISINTEGRATING REGION BY ENERGIZING RING-SHAPED TRANSDUCERS, AND HYPERTHERMIA CURING SYSTEM

This application is a continuation of application Ser. No. 08/029,659, filed Mar. 10, 1993, now abandoned.

BACKGROUND OF THE INVENTION

1. Field of the Invention

The present invention generally relates to a shock wave generating apparatus capable of disintegrating an object within a biological object under medical examination, e.g., a cancer cell, and a concretion by utilizing focused energy of shock waves. More specifically, the present invention is directed to a shock wave generating apparatus capable of generating a wide concretion-disintegrating region by employing ring-shaped transducers, and also to a hyperthermia curing system.

2. Description of the Prior Art

Various types of shock wave generating apparatuses have been proposed, such as those described in Japanese KOKAI (Disclosure) patent application No. 62-49843 (1987). In FIG. 1, for example, there is shown, a sectional view of an ultrasonic wave applicator of one conventional shock wave generating apparatus.

The construction of this ultrasonic wave applicator 1 is as follows. A through hole having a predetermined shape is formed in a center portion of the applicator 1. A vibrating element (e.g., a piezoelectric transducer element) 2 is spherically formed and a backing material 3 is uniformly adhered to a rear surface of this spherical vibrating element 2. An imaging ultrasonic probe 4 is positioned in such a manner that a transmitting/receiving wave front (ultrasonic array) 4a is located at the curved surface which is identical to the shock wave transmitting/receiving wave front of the vibrating element 2, or rearward of the aforementioned wave front. Furthermore, this ultrasonic wave applicator 1 includes a water bag 5 containing water as a coupling medium for the ultrasonic waves. Reference numeral 8 indicates a biological body under medical examination.

To disintegrate a concretion or calculus within a biological body by utilizing the above-described conventional shock wave generating apparatus, the focal point of the generated shock wave must be pointed to this concretion, which action will hereinafter be referred to as "a positioning of a focal point". As apparent from FIG. 2A, a shape of this focal point is very small, like a "pinpoint focused region".

FIG. 2A to 2C illustrate relationships between the shock wave front and focused region in the conventional shock wave generating apparatus shown in FIG. 1.

In FIG. 2A, reference numeral 7 indicates a single focused region of the shock wave transmitted from the vibrating element 2. This vibrating element 2 is subdivided into six portions as illustrated in FIG. 2B, and the six positions are arranged in a spherical form as represented in FIG. 2A. It should be noted that only one focused region 7 is formed from six element portions "a" to "f". FIG. 2C is an illustration of the focused region 7 as viewed from the transmission direction of the shock wave toward an object 8 to be disintegrated.

Assuming now that an area indicative of a half value of a peak pressure produced by a shock wave transmitted from a vibrating element is defined as the above-described pinpoint focused region τ, this single focused region 7 is geometrically determined by the diameter of the spherical body and the aperture of the vibrating element 2. As apparent from FIG. 2C, Since a size of this pinpoint focused region 7 is very small as compared with the object 8 to be disintegrated within the biological body, the calculus disintegrating efficiency by the shock wave is considerably lowered, which necessarily requires a large quantity of time so as to completely disintegrate the object 8.

To solve the above-described problem (i.e., lengthy disintegrating time) associated with such a prior art shock wave generating system, very recently, a very novel and epoch-making shock wave generating system has been patented under U.S. Pat. No. 5,062,412 on Nov. 5, 1981 to Okazaki entitled "SHOCK WAVE GENERATING APPARATUS FORMING WIDE CONCRETION-DISINTEGRATING REGION BY FOCUSED SHOCK WAVE".

Simply speaking, in accordance with this U.S. Patent, a wide focused region is formed by energizing a plurality of transducers in such a manner that a plurality of pinpoint focal points are formed and positioned adjacent to each other.

The featured structure of this U.S. Patent will now be summarized with reference to FIGS. 3A to 3C.

Referring now to FIGS. 3A to 3C, the shock wave generating means 15 will be described in detail. FIGS. 3A to 3C pictorially represent the relationships between the shock wave front and the focused regions in the shock wave generating apparatus. As illustrated in FIGS. 3A and 3B, this shock wave generating means 15 is constructed in such a manner that a plurality of ultrasonic vibrating elements, e.g., 14 pieces of the piezoelectric transducer elements are arranged in an endless form, and the wave front of the generated shock wave is a substantially spherical shape. The shock wave generating means 15 includes a plurality of vibrating element groups, e.g., 7 groups, from which the geometrically focused shock waves are produced. That is to say, a first vibrating element group 10a is formed by one pair of vibrating elements denoted by "a" in FIG. 3B; a second vibrating element group 10b is formed by a pair of vibrating elements indicated by "b" in FIG. 3B a sixth vibrating element group 10f is constructed of a pair of vibrating elements denoted by "f" shown in FIG. 3B; and furthermore a seventh vibrating element 10g group is formed by one pair of vibrating elements denoted by "g" shown in FIG. 3B. As illustrated in FIG. 3B, one pair of vibrating elements "a" to "g" constituting the respective vibrating element groups 10a to 10g are positioned on diagonal lines. It should be noted that for the sake of the simplicity, arrows for denoting the respective vibrating element groups 10b to 10g are attached only to one vibrating element constructing the respective element groups.

The vibrating elements for producing the shock waves, may for instance, be a piezoelectric transducer elements.

FIG. 3C illustrates the respective focused regions which are simultaneously formed by driving the vibrating element groups 10a to 10g, as viewed in the shock wave transmission direction. It should be noted that although the shapes of these focused regions are circular, the actual shapes thereof are elliptic or oval.

As previously described, one pair of vibrating elements "a" and "a" constituting the first vibrating element group 10a are positioned in such a manner that the shock waves transmitted from these vibrating elements "a" and "a" are synthesized at a first position geometrically defined so as to form a first focused region 11a. Another pair of vibrating elements "b" and "b" constituting the second vibrating element group 10b are positioned in such a manner that the shock waves transmitted from these vibrating elements "b" and "b" are synthesized at a second position geometrically defined, thereby forming a second focused region 11b. Similarly, the respective vibrating elements for constituting the third, fourth, fifth, sixth and seventh vibrating element groups 10c, 10d, 10e, 10f, and 10g are so arranged as to form third to seventh focused regions 11c to 11g, respectively, at geometrically defined areas. These focused regions 11a to 11g are formed at the same time under the condition that the simultaneously formed focused regions are juxtaposed with each other, as illustrated in FIG. 3C. As a consequence, a synthesized effective focused region by the first through seventh focused regions 11a to 11g is about 7 times larger than each of these focused regions 11a to 11g. In other words, since the resultant effective focused region simultaneously formed by juxtaposing a plurality of focused regions 11a to 11g with each other can be made considerably larger than the pinpoint focal point 7 (see FIG. 2C) formed in the shock wave generating apparatus previously described. The effective disintegrating efficiency for the object to be disintegrated can thus be improved according to this U.S. Patent.

However, the above-described U.S. Patent has a lack of practical utilization. First, the same number of delay circuits, e.g., 7 delay circuit groups, are required as that of the transducer channels, resulting in a very complex delay control. Secondly, it is desirable from a practical standpoint that a calculus-disintegration treatment should be performed with irradiating shock waves having an optimum beam width (i.e., a size of a focused region along an aperture direction) relative to the calculus, taking account of various conditions of this calculus. Also, to disintegrate a calculus or stone, a peak pressure of shock wave pulses, or a temperature of focused energy of a continuous wave must be set to be higher than a threshold value. Nevertheless, if an excessive peak pressure is administered to a biological body, it may feel pain and may incur medical risk.

Furthermore, sizes of a focused region are preferably varied along not only an aperture direction, but also a depth direction in such a wide focused region type shock wave generating system, or hyperthermia curing system.

SUMMARY OF THE INVENTION

The present invention has been developed in order to achieve the above-described desirable feature, or improve the functions of the last-mentioned conventional shock wave generating apparatus, and therefore, has an object to provide a shock wave generating system capable of forming a wide focused region of the shook waves using a simple structure.

Another object of the present invention is to provide a shock wave generating system capable of readily controlling a size of such a wide focused region along an aperture direction, depending upon a disintegrated condition of a concretion.

Another object of the present invention is to provide a shock wave generating system capable of easily controlling a focused region of shock waves along a depth direction of a calculus to be disintegrated.

A further object of the present invention is to provide a medically safe shock-wave generating system with a variable effective region of shock waves with respect to a calculus.

A still further object of the present invention is to provide an ultrasonic hyperthermia apparatus capable of readily controlling an irradiating range of focused energy by a continuous wave, depending upon a size of a curing object within a biological body under medical examination.

To achieve the above-described objects, a shock wave generating system, according to one aspect of the present invention, comprises:

shock wave generating means (3) having a plurality of shock-wave generating elements (3a:100a:200a) and driving means (6:10:13) for separately driving said plurality of shock-wave generating elements (3a:100a:200a) by controlling at least delay times ($\tau_1:\tau_0$) to produce a plurality of shock waves in such a manner that a dimension of a focused region (70:80) synthesized from a plurality of different focal points formed by said plurality of shock waves, is varied in accordance with a dimension of a concretion to be which is present in a biological body (P) under medical examination.

Furthermore, to achieve the last object, a continuous wave hyperthermia apparatus, according to another aspect of the present invention, comprises:

ultrasonic pulse generating means having a plurality of ultrasonic-pulse generating elements; and driving means (6:10:13) for separately driving said plurality of ultrasonic-pulse generating elements by controlling at least delay times ($\tau_1:\tau_0$) to produce a plurality of ultrasonic pulses in such a manner that a dimension of a focused region (70:80) synthesized from a plurality of different focal points formed by said plurality of ultrasonic pulses, is varied in accordance with a dimension of an object within a biological body (P), to be medically cured.

BRIEF DESCRIPTION OF THE DRAWINGS

For a better understanding of the present invention, reference is made to the following description in conjunction with the accompanying drawings, in which;

FIGS. 3A to 3C are Illustrations for schematically explaining the formation of the plural focused regions of the shock waves by a second conventional shock wave apparatus:

FIG. 4 schematically shows an arrangement of a basic shock wave generating system according to one aspect of the present invention:

FIGS. 12A and 12B are illustrations for explaining how to form wide-narrow focused regions 70 an 80 by the first shock wave generating system of FIG. 10;

FIG. 13A to 17b schematically represent variation in sizes of the focused regions $SW_1$ to $SW_4$ formed in the first shock wave generating system of FIG. 10;

DETAILED DESCRIPTION OF THE PREFERRED EMBODIMENTS

ARRANGEMENT/OPERATION OF BASIC SHOCK-WAVE GENERATING SYSTEM

Figure 1:
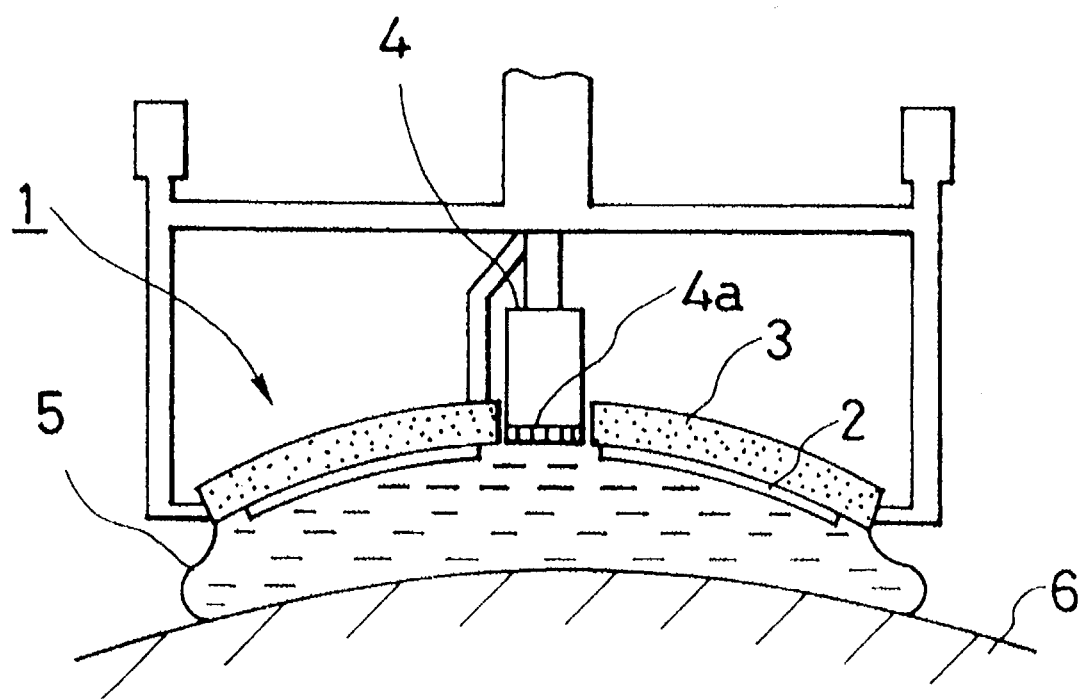
FIG. 1 is a sectional view of an ultrasonic pulse applicator employed in a first conventional shock wave generating apparatus.
Figure 2A:
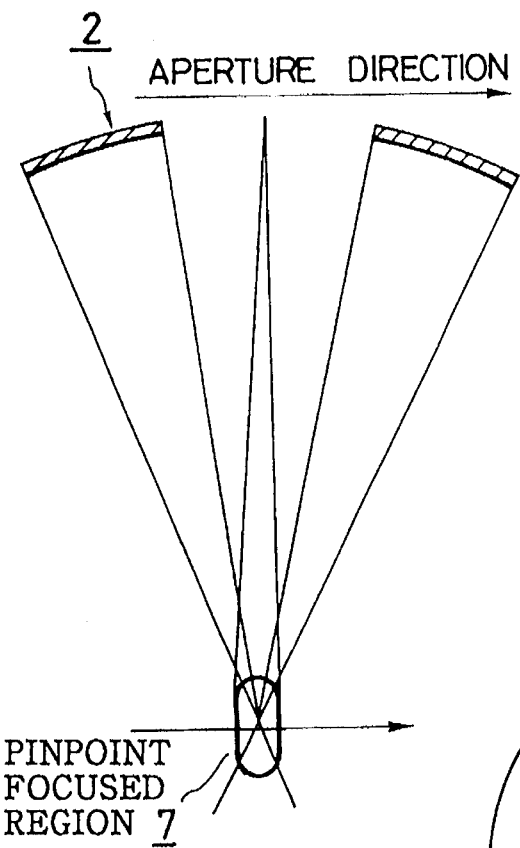
FIGS. 2A to 2C are illustrations for schematically explaining the formation of the single focused region of the shock waves produced by the first conventional ultrasonic pulse applicator shown in FIG. 1.
Figure 2B:
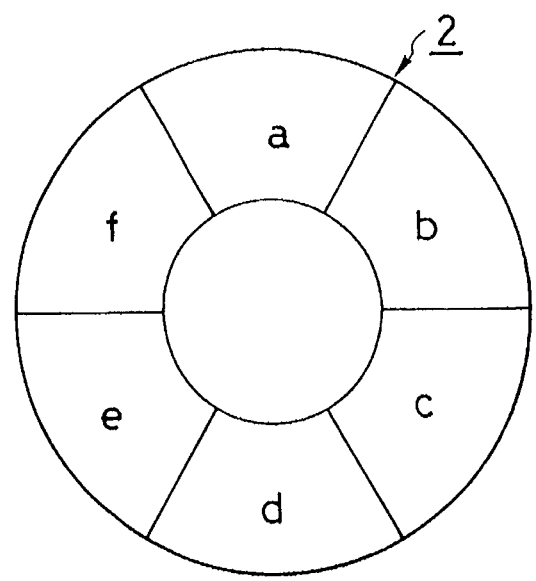
Figure 2C:
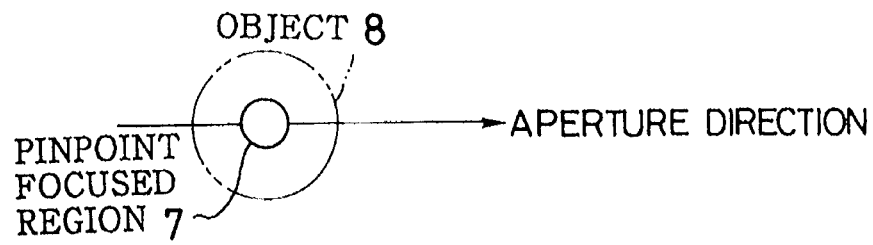
Figure 5:
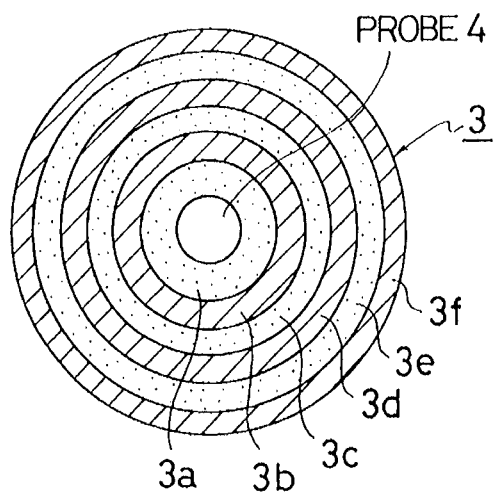
FIG. 5 schematically illustrates 6 ring-shaped transducer elements employed in the basic shock wave generator of FIG. 4, and FIG. 6 schematically shows a relationship among a focused position, geometrical focus points and shock waves transmitted from the ring-shaped transducer elements of FIG. 5.
Figure 7:
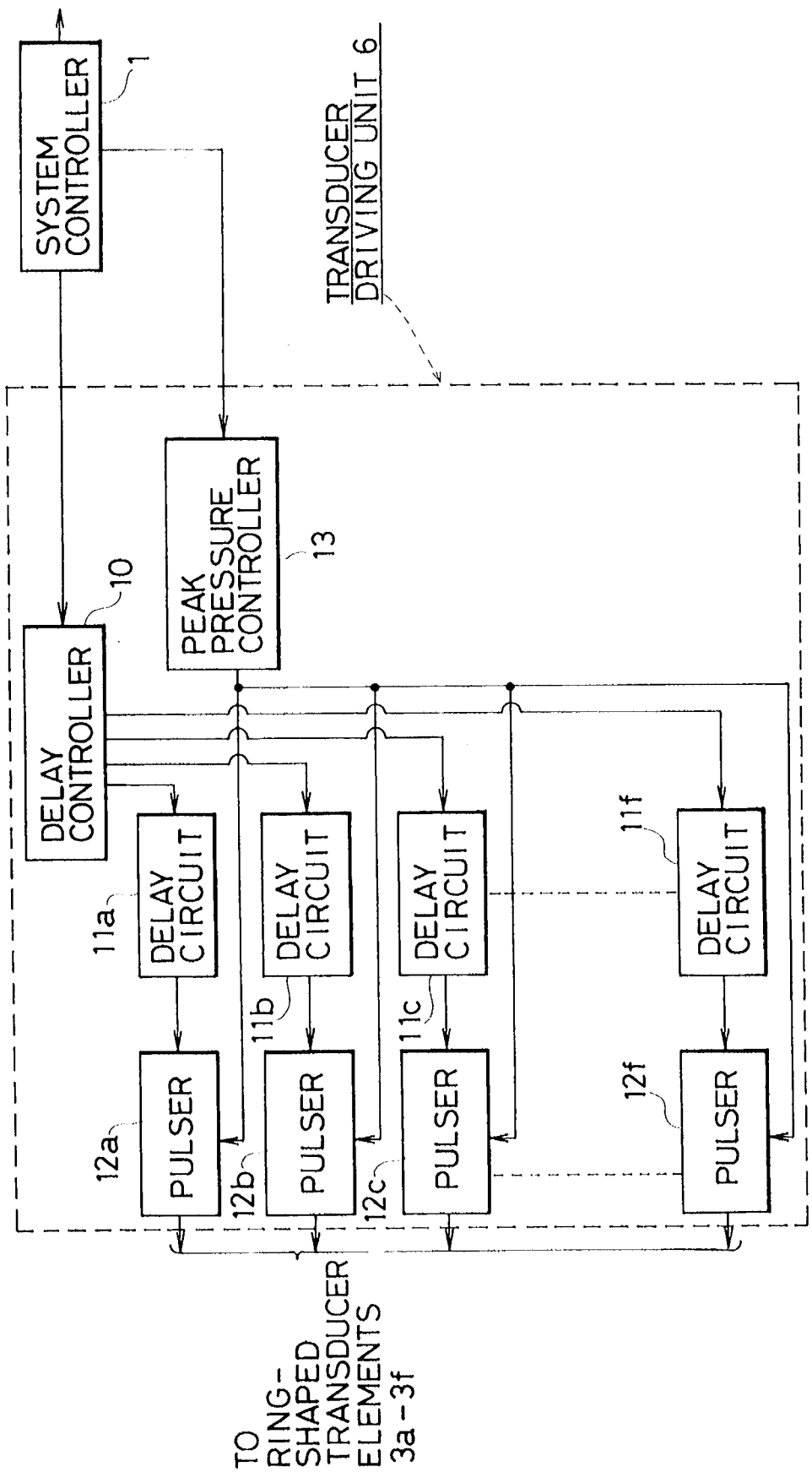
FIG. 7 is a schematic block diagram of an internal circuit of the transducer driving unit 6 shown in FIG. 4.

Referring now to FIGS. 4, 5 and 7, arrangements of a basic shock-wave generating system according to the present invention and of a shock wave applicator employed in this basic shock-wave generating system will be described.

FIG. 4 schematically represents an overall arrangement of this basic shock-wave generating system.

This basic shock-wave generating system is mainly arranged by a system controller 1 for controlling an overall circuit element of this system, an ultrasonic imaging unit 2 for ultrasonic-scanning a patient "P" to obtain an ultrasonic image of the patient and also for displaying this ultrasonic image and a marker indicative of a focused position of shock waves, a shock wave generating source 3 installed within a water vessel, and an applicator 5 equipped with an ultrasonic imaging probe 4. Furthermore, the basic shock wave generating system includes a transducer driving unit 8 for applying a high voltage, e.g., 1 to 3 kV, having a frequency of, for example, 500 kHz to a transducer element (which will be discussed later) to produce a shock wave, a position controller 9 for controlling a positional-relationship between the ultrasonic imaging probe 4 and the shock wave generating source 3 along a vertical direction, as viewed in FIG, 4, and a couch 8 for mounting the patient "p" thereon, FIG. 5 is a plan view of the above-described shock wave generating source 3 equipped with the ultrasonic imaging probe 4 positioned at a center thereof. As seen from FIG. 5, this shock wave generating source 3 is constructed of 6 ring-shaped transducer elements "3a" to "3f" arranged in a concentric circular form. Also as seen from FIG. 6, a side view of the shock wave generating source 3 is spherical (as will be discussed-later). It should be noted that although 6 ring-shaped transducer elements "3a" to "3f" are employed as the shock wave generating source 3 for the sake of clarity sets of, in principle, at least 2 sets of ring-shaped (or similarly shaped) transducer elements may be used as the shock wave generating source 3. Piezoelectric transducer elements may be used as the ring-shaped transducer elements. These ring-shaped transducer elements "3a" to "3f" are adhered to each other, but can be independently driven by the transducer drive unit 6.

Figure 8:
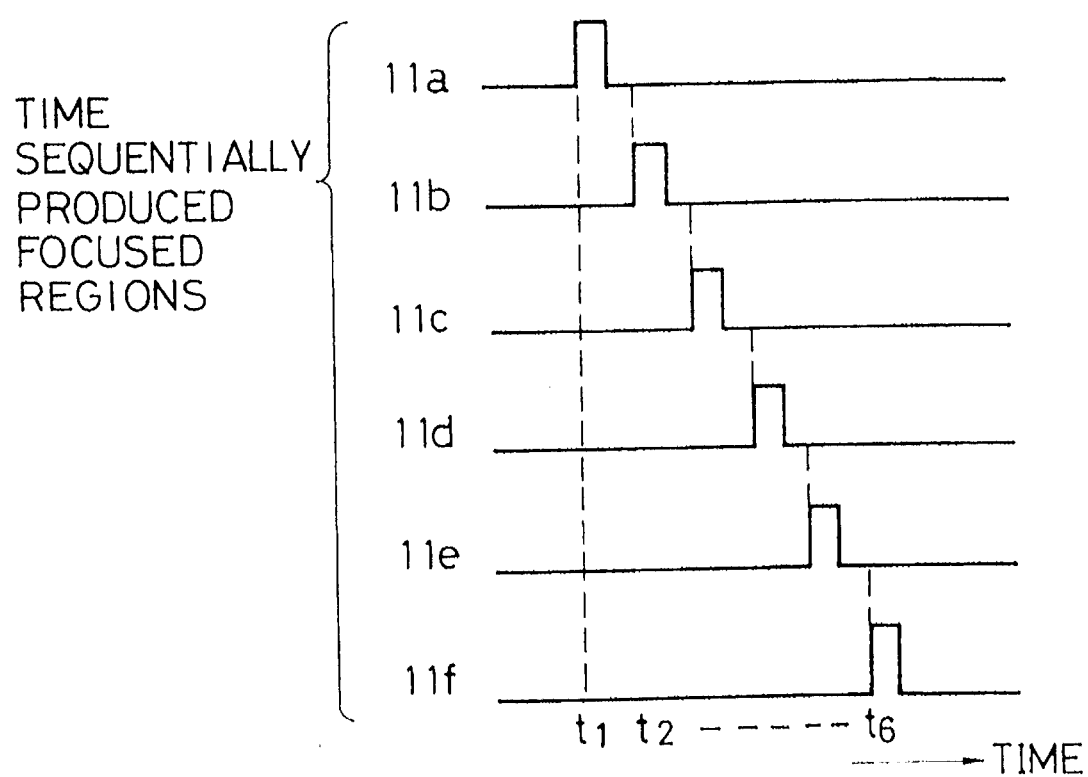
FIG. 8 schematically shows a timing chart of drive pulses for the ring-shaped transducer elements indicated in FIG. 5.

FIG. 7 is a schematic block diagram of an internal circuit arrangement of the transducer driving unit 6, and FIG. 8 shows a timing chart of pulser outputs for driving the ring-shaped Transducer elements 3a to 3f.

In the transducer driving unit 6, 6 pulsers "12a" to "12f" are provided to apply a high-voltage pulse voltage to each of the 6 ring-shaped transducer elements "3a" to "3f" (see FIG. 5). A delay controller 10 is employed so as to control the driving times of the pulsers 12a to 12f in response to a delay control signal supplied from the system controller 1. Similarly, 6 delay circuits 11a to 11f are interposed between the respective pulsers 12a to 12f and the delay controller 10 so that the driving times of the pulsers 12a to 12f are controlled to produce 6×6 different shock-wave focused points (as will be discussed later in more detail) under control of the delay controller 10. The driving pulse signals are time-sequentially delayed as represented in FIG. 8, so that for instance, a first driving pulse signal is produced by the first delay circuit 11a from the first pulser 12a at a time instant "t1", and a sixth driving pulse signal is produced by the sixth delay circuit 11f by the sixth pulser 12f at a time instant "$t_0$" later than the time instant "$t_1$".

Furthermore, a peak pressure controller 18 is provided to control the voltages of the driving pulse signals produced from the pulsers 12a to 12f under control of the system controller 1.

In accordance with a major feature of this basic shock wave generating system, a synthesized focused region formed by 6 shock waves is variable by the delay controller 10. This focused region is formed by synthesizing the 6×6 geometrical focus points with each other, which are produced by driving the respective transducer elements "3a" to "3f" at the above-described different driving times (see FIGS. 6 and 8). In other words, depths of the focused points of the 6 shock waves are slightly changed to vary the size (width) of the synthesized focused region along the aperture direction, namely the horizontal direction of FIG. 6. Moreover, the size (depth) of the synthesized focused region may be changed along the depth direction of the shock wave, namely the vertical direction of FIG. 6.

Figure 6:
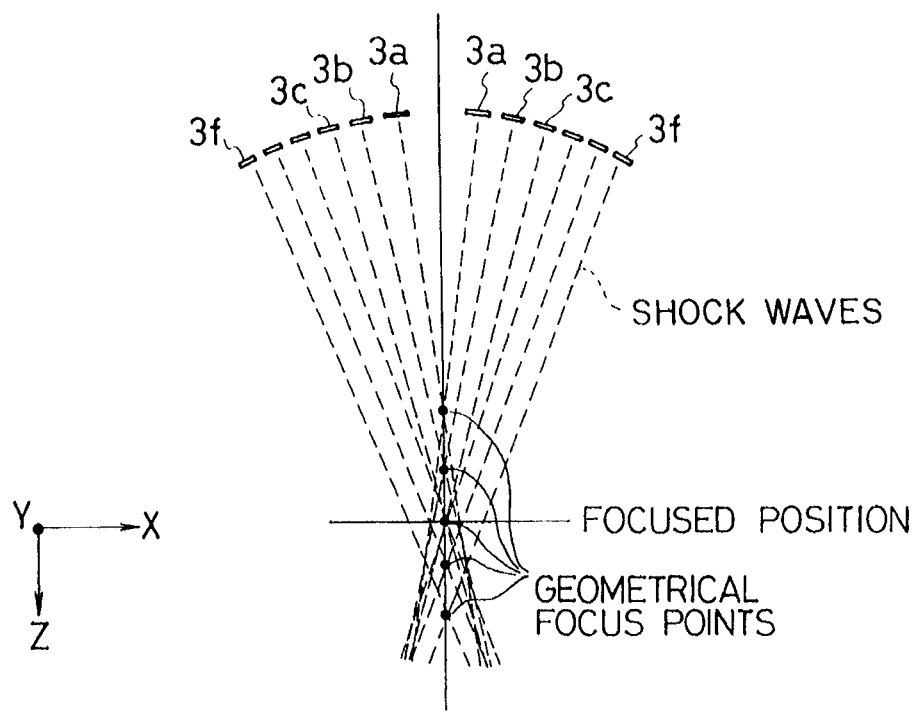
Figure 9A:
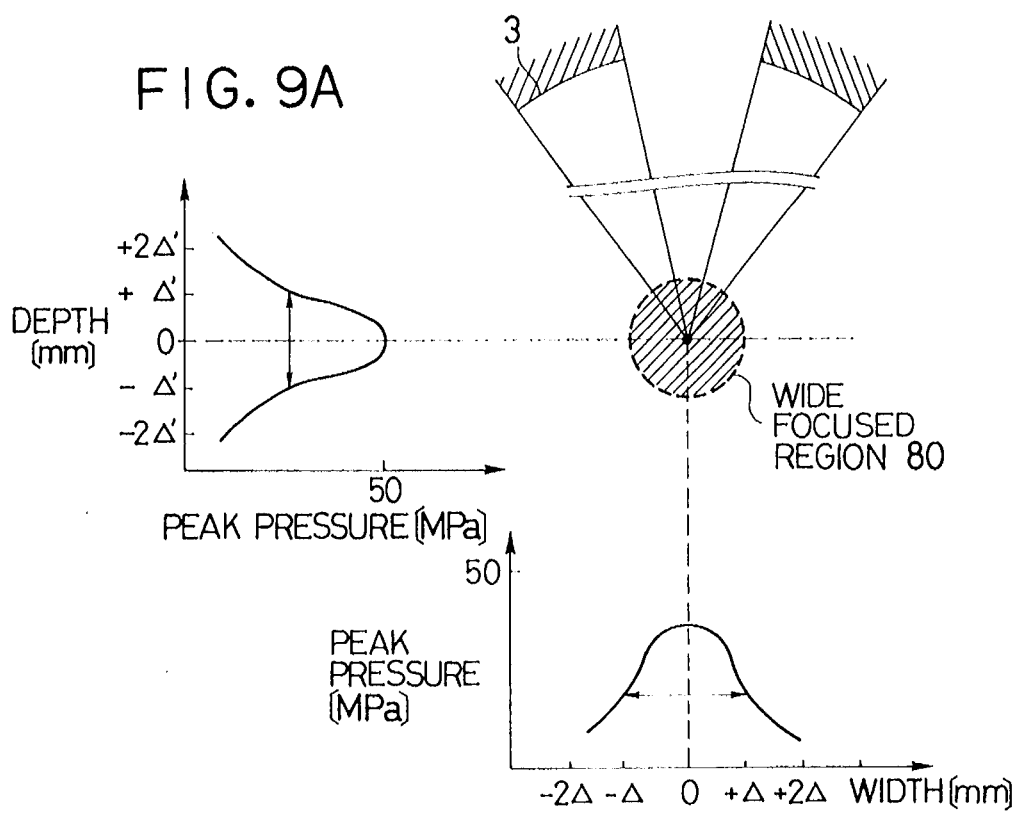
FIGS. 9A and 9B schematically illustrate formations of wide-narrow focused regions by the basic shock wave generating system of FIG. 4.

FIG. 9A schematically shows a wide focused region 80 formed at the focused position of FIG. 6 from the six transducer elements "3a" to "3f" along both the width (X) direction and the depth (Z) direction in the basic shock wave generating system of FIG. 4.

Figure 9B:
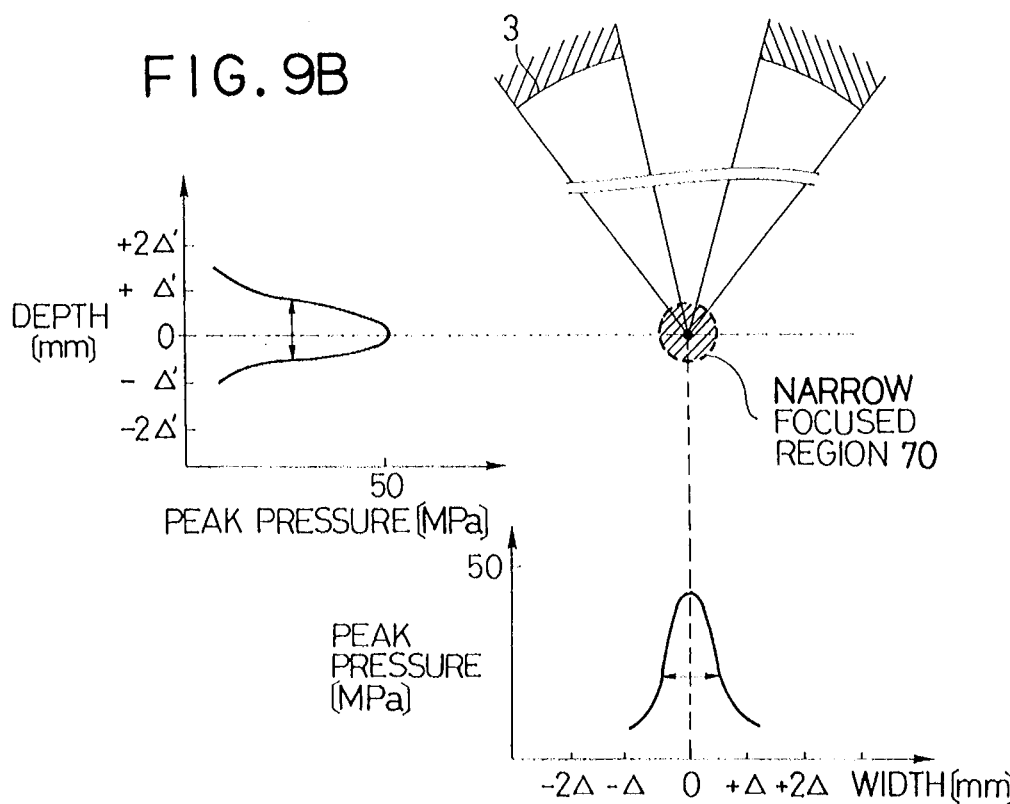

FIG. 9B schematically represents a narrow focused region 70 similarly formed at the focused position of FIG. 6 from the six transducer elements along both the width direction and the depth direction.

As apparent from FIGS. 9A and 9B, according to this basic shock wave generating system, the widths of the focused regions 70 and 80 may be varied not only along the horizontal (X or width) direction, but also along the vertical (Z or depth) direction.

ARRANGEMENT OF FIRST SHOCK WAVE GENERATING SYSTEM

Figure 10:
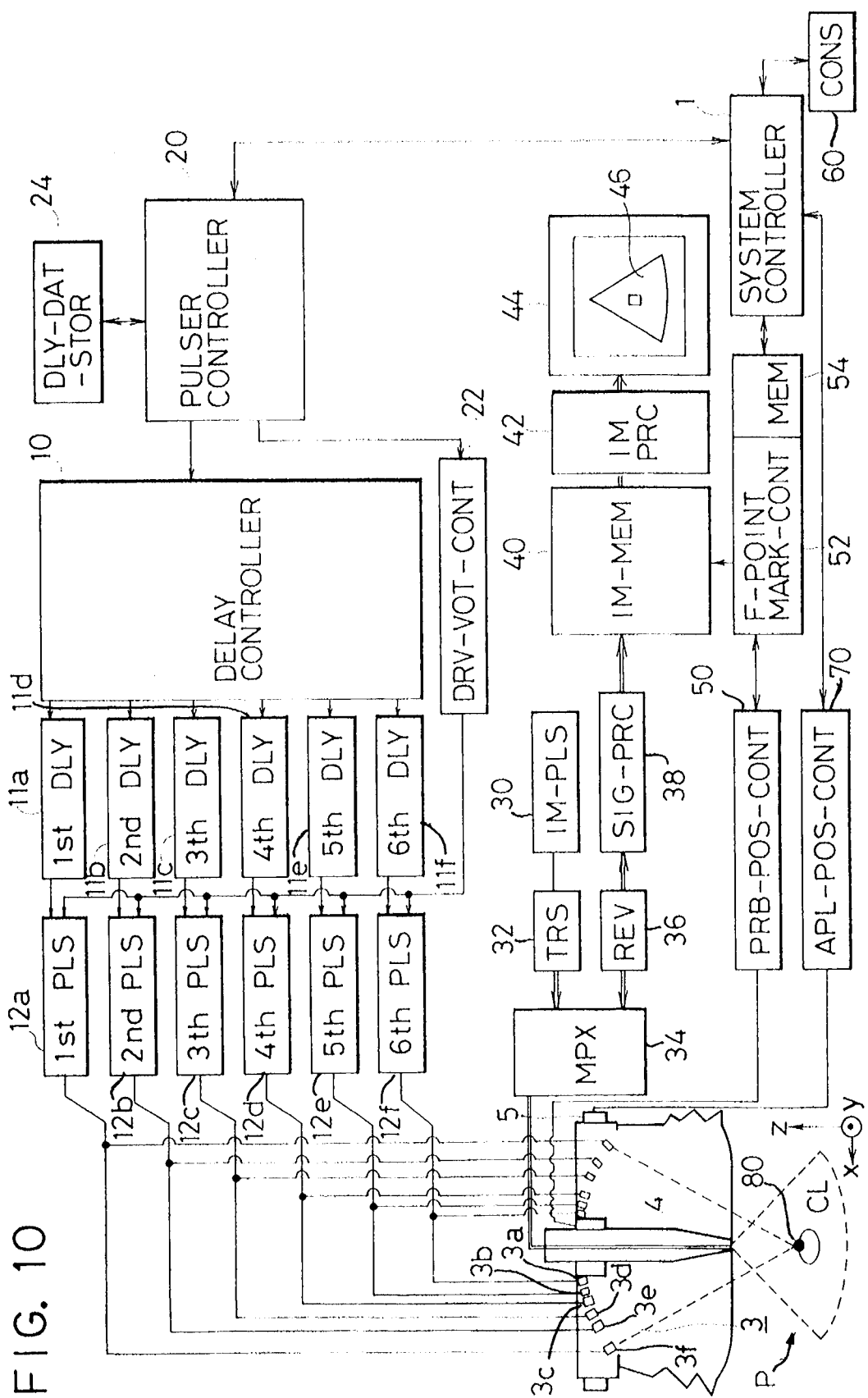
FIG. 10 is a schematic block diagram of an overall arrangement of a shock wave generating system according to a first preferred embodiment of the present invention.

In FIG. 10, there is shown an overall arrangement of a shock wave generating system according to a first preferred embodiment of the present invention, Since this first system is similar to the previously-explained basic shock wave generating system of FIG. 4, only different circuit arrangements will be explained.

In the circuit arrangement of FIG. 10, a pulser controller 20 is connected to the delay controller 10 (also see FIG. 7) and a drive voltage controller 22. The drive voltage controller 22 is connected to the first to sixth pulsers 12a to 12f.

A delay data storage unit 24 is connected to the pulser controller 20. The delay data storage unit 24 stores delay data which are supplied via the pulser controller 20 to the delay controller 10, so that the drive pulse signals are delayed by preselected delay times in the relevant first to sixth delay circuits 11a to 11f. Then, the drive voltage controller 22 corresponds to the peak pressure controller 13 of FIG. 7.

Furthermore, an imaging pulser 30 is employed to produce a low-voltage drive pulse signal which will then be supplied to a transmitter circuit 32. As a result, the patient "P" is ultrasonically scanned by the imaging probe 4 energized by the transmitter circuit 32 via a multiplexer 34. Echo signals from the probe 4 are received via the multiplexer 34 to a receiver circuit 36 and a signal processor 38, so that ultrasonic imaging signals about the scanned interior portion of the patient "P" are produced. Thereafter, these ultrasonic imaging signals are temporarily stored into an image memory 40, and processed in an image processor 42 to obtain B-mode ultrasonic image data. Base upon this B-mode ultrasonic image data, a B-mode ultrasonic image of the scanned patient "P" is displayed on a monitor 44.

A probe position controller 50 is connected to the probe 4, and also to a focal-point marker controller 52 with a memory 54.

Further, an applicator position controller 70 is connected to the applicator 5, and an operation console 60 is connected to the system controller 1.

PRACTICAL DATA OF RING-SHAPED TRANSDUCER ELEMENTS

Each of the ring-shaped transducer elements "3a" to "3f" exhibits the following actual dimensions, for example, a diameter of the first ring-shaped transducer element "3a" is preferably selected to be approximately 138 mm, and a diameter of the sixth ring-shaped transducer element "3f" is preferably about 300 mm.

FORMING OF WIDE FOCUSED REGION BY FIRST SHOCK WAVE GENERATING APPARATUS

Figure 11:
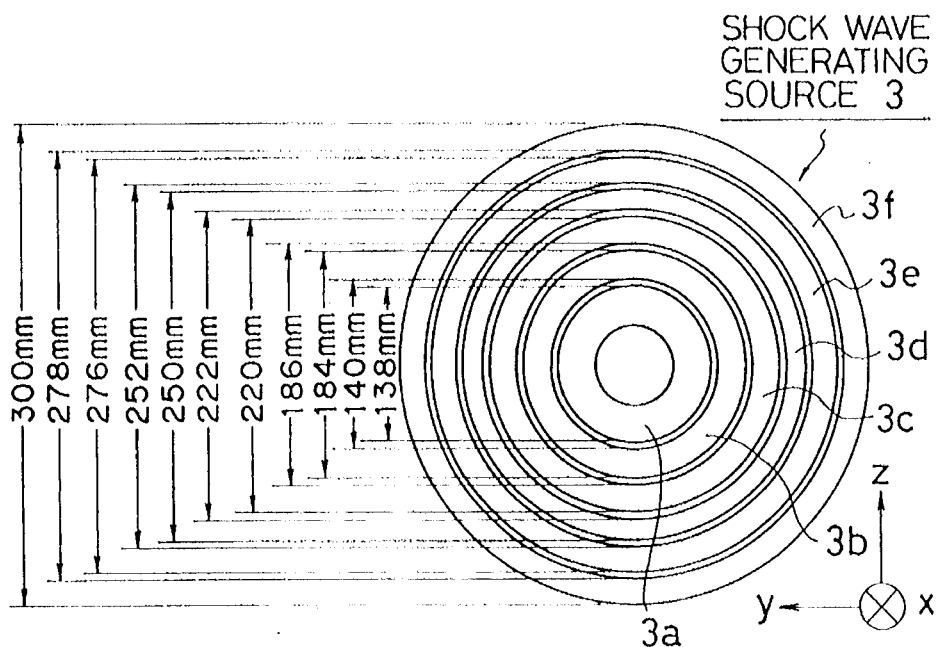
FIG. 11 schematically illustrates ring-shaped transducer elements used In the first shock wave generating system of FIG. 10.

FIG. 11 schematically shows the 6 ring-shaped transducer elements "3a" to "3f" of the shock wave generating source 3 with practical ring sizes. As represented in FIG. 11, the outermost ring-shaped transducer element "3f" has a diameter of approximately 300 mm, whereas the innermost ring-shaped transducer element "3a" has a diameter of about 138 mm. These transducer elements "3a" to "3f" are arranged so as to form a spherical cross-sectional shape, when viewed in a sectional direction.

For a better understanding of the features of the present invention, formations of two focused regions 70 and 80 having different sizes (widths) will now be explained with reference to FIGS. 12A and 12B.

Figure 12A:
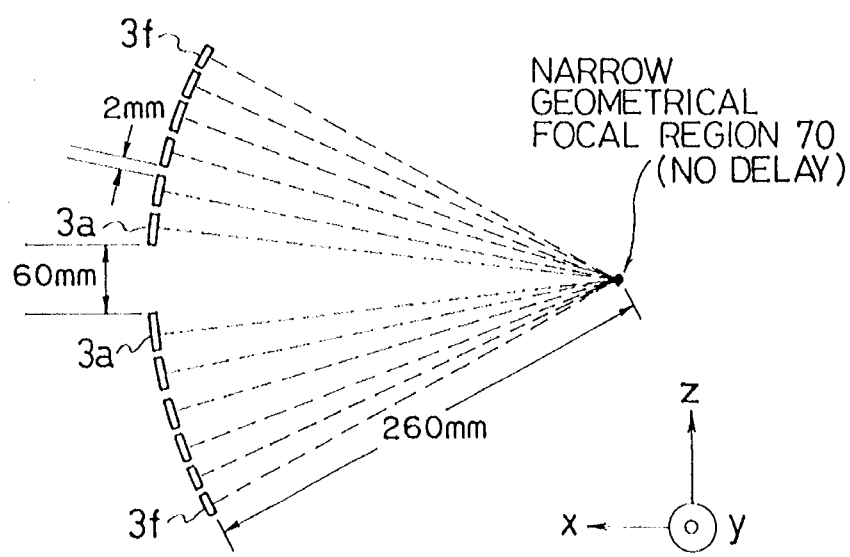

First, FIG. 12A represents the formation of a narrow geometrical focused region 70 by the first shock wave generating system. When all of the ring-shaped transducer elements "3a" to "3f" are driven at substantially the same timing, with no delays, such a narrow geometrical focal point 70 can be produced at a position apart from the respective transducer elements "3a" to "3f" by 260 mm.

By way of contrast, according to another focal region formation by the first shock wave generating system shown in FIG. 10, the respective ring-shaped transducer elements "3a" to "3f" are driven at different timings, namely under different delay times "$t_1$" to "$t_0$", as illustrated in FIGS. 12B and 8, by the first pulser "12a" to the sixth pulser "12f" of FIG. 10. For Instance, as shown in FIG. 12B, the first (innermost) transducer element 3a is driven at a first drive timing "$t_1$" by the sixth pulser 12f. This first drive pulse is illustrated in the sixth pulser 12f of FIG. 12B.

As a consequence, precisely speaking, 36 geometrical focal points are formed at different positions adjacent to each other, resulting in a formation of such a wide geometrically focused region 80. That is, a size or width of this focused region 80 is considerably greater, or wider than That of the first-mentioned focal point 70.

OPERATION OF FIRST SHOCK WAVE GENERATING SYSTEM

Referring now to the overall arrangement of the first shock wave generating system, an operation thereof and especially a formation of wide focused region 80 will be described.

Figure 13A:
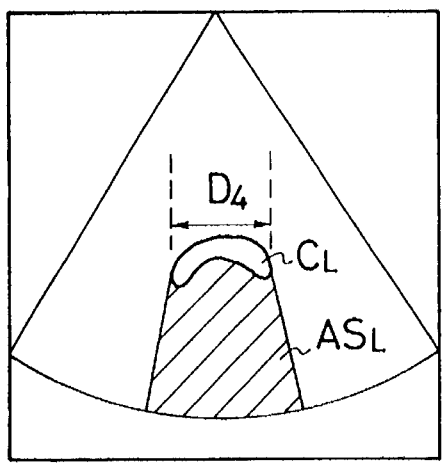
Figure 14A:
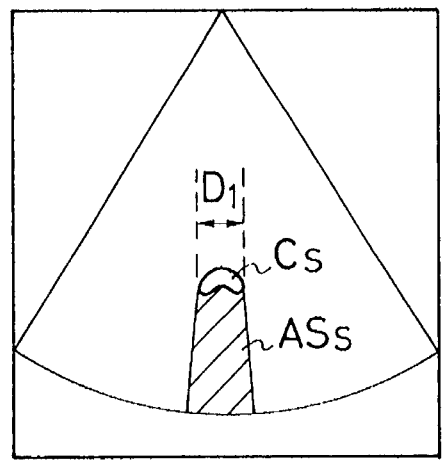
Figure 13B:
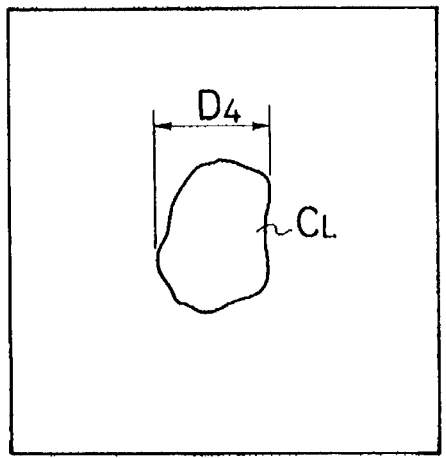
Figure 14B:
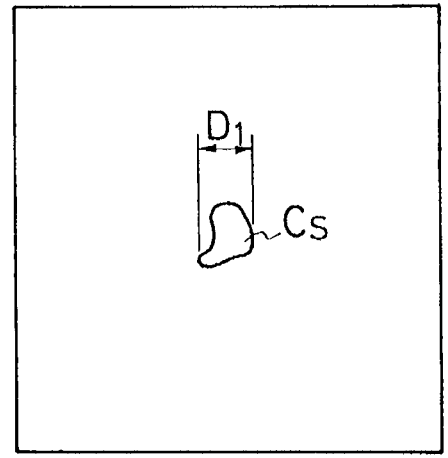

First, as schematically illustrated in FIGS. 13A, 13B, 14A and 14B, it is assumed that two different types of concretion "$C_L$" and "$C_S$" are present in the patient "P". FIG. 13A represents a B-mode ultrasonic image of the large concretion "$C_L$". Since the size of this concretion "$C_L$" is large, a large acoustic shadow "$AS_L$" appears in this B-mode image. To the contrary, since the size of the small concretion "$C_S$" is small as shown in a B-mode ultrasonic image of FIG. 14A, a small acoustic shadow "$AS_S$" appears therein. As apparent from FIGS. 13A and 14A, side views of these concretions "$C_L$" and "$C_S$" are shown, whereas top views thereof are represented in FIGS. 13B and 14B.

As a result, according to the feature of the first shock wave generating system the size (width) of the focused region 80 may be varied by properly changing the delay times "$T_1$" to "$T_0$" of the first to sixth delay circuits 11a to 11f and/or properly changing the drive pulse voltages of the first to sixth transducer elements "3a" to "3f", depending upon the sizes of the concretions "$C_L$" and "$C_S$".

To achieve a formation of the variably focused region 80, the sizes of the focused regions 70 and 80 are determined in this preferred embodiment as shown in FIG. 15. For instance, since the diameter of the large concretion "$C_L$" is $D_4$ as shown in FIG. 13A and 13B the size of focused region is selected to be "$SW_4$" in FIG. 15. Similarly, the size of the focused region is selected to be "SW1" in FIG. 15 for the small concretion "$C_S$".

Then, with respect to the large focused region "SW4", the delay time data for forming such a region are previously stored in the delay data storage unit 24 of FIG. 10. These delay time data are read out from this storage unit 24 and then supplied to the delay controller 10. As shown in FIG. 16A, first to sixth delay times "$\tau_1$" to "$\tau_0$" are selected to be 0, 0.4, 0.8, 1.1, 1.7 and 2.6 µS under control of the delay controller 10. Also, the drive pulse voltage for the transducer elements "3a" to "3f" is set to V4. When all of these transducer elements "3a" to "3f" are sequentially driven by the first to sixth pulsers "12a" to "12f" at predetermined delay times "$\tau_1$" to "$\tau_4$", respectively, under control of the pulser controller 20, 6 shock waves are produced ("3a" to "3f") and then focused onto 36 focal points, which form the wide focused region 80 (see FIG. 12B), Precisely speaking, a synthesized focused region is formed under such a condition that a width "$W_4$" thereof is approximately 5 mm along the X-direction and a peak pressure "$P_{max1}$" thereof is about 70 MPa as shown in FIG. 16B.

On the other hand, when the size of the small concretion "$C_S$" is "$D_1$" (diameter), or when the reduced size of the large concretion "$C_L$" after disintegration becomes "$D_1$", the size of the focused region is selected, or changed into "$SW_1$", so that the delay times "$\tau_1$" to "$\tau_6$" are set to 0 (zero) μS and the voltage of the drive pulses is selected to be "$V_1$" ($=V_4$), as shown in FIG. 17A.

Then, the synthesized focused region is formed under such a condition that a width "$W_1$" thereof is approximately 2 mm, and a peak pressure "$P_{max1}$" is about 70 MPa as shown in FIG. 17B.

The selection of the sizes $SW_1$, $SW_4$ of the focused region is performed by the console unit 60 (see FIG. 10).

Before performing the above-described shock wave generation, namely a disintegration of a concretion "$C_L$", "$C_S$", the following B-mode imaging operation and marker displaying operation are carried out.

That is, after the patient "P" has been laid on the couch 8 (see FIG. 4), the ultrasonic probe 4 is operated under control of the imaging pulser 30 via the transmitter circuit 32, the receiver circuit 36 and the signal processor 38 so as to acquire B-mode image data of a certain slice plane within the patient "P". Then, the acquired B-mode image data are temporarily stored in the image memory 40, and thereafter processed in the image processor 42, so that the B-mode ultrasonic image of the scanned slice plane within the patient "P" is displayed on the monitor 44.

On the other hand, to display a focal-point marker 48 on the concretion "$C_L$" or "$C_S$" displayed in the B-mode image of the monitor 44, the ultrasonic probe 4 is positionally shifted by the probe position controller 50 under control of the focal-point marker controller 52. The data about the focal point marker 48 is supplied to the image memory 40 to be superimposed on the B-mode image data therein. Accordingly, the calculus "$C_L$" or "$C_S$" is positionally coincident with this focal-point marker 46 on the display screen of the monitor 44, so that the size of the calculus "$C_L$", "$C_S$" can be confirmed to determine the size $SW_1$, $SW_4$ of the focused region using the console unit 60.

The transducer elements "$3a$" to "$3f$" of the shock wave applicator 5 can be positionally moved under control of the applicator position control 70.

As previously stated, according to the first shock wave generating system shown in FIG. 10, not only the horizontal width ($W_1$ to $W_4$) of The focused region along the X-direction (horizontal direction of FIG. 19) may be varied by properly selecting the delay times for driving the transducer elements "$3a$" to "$3f$", but also the vertical width of the focused region along Z-direction (vertical, or depth direction of FIG. 10) may be varied by properly selecting the delay times and the drive voltages controlled by the drive voltage controller 22.

ULTRASONIC HYPERTHERMIA SYSTEM

Figure 20:
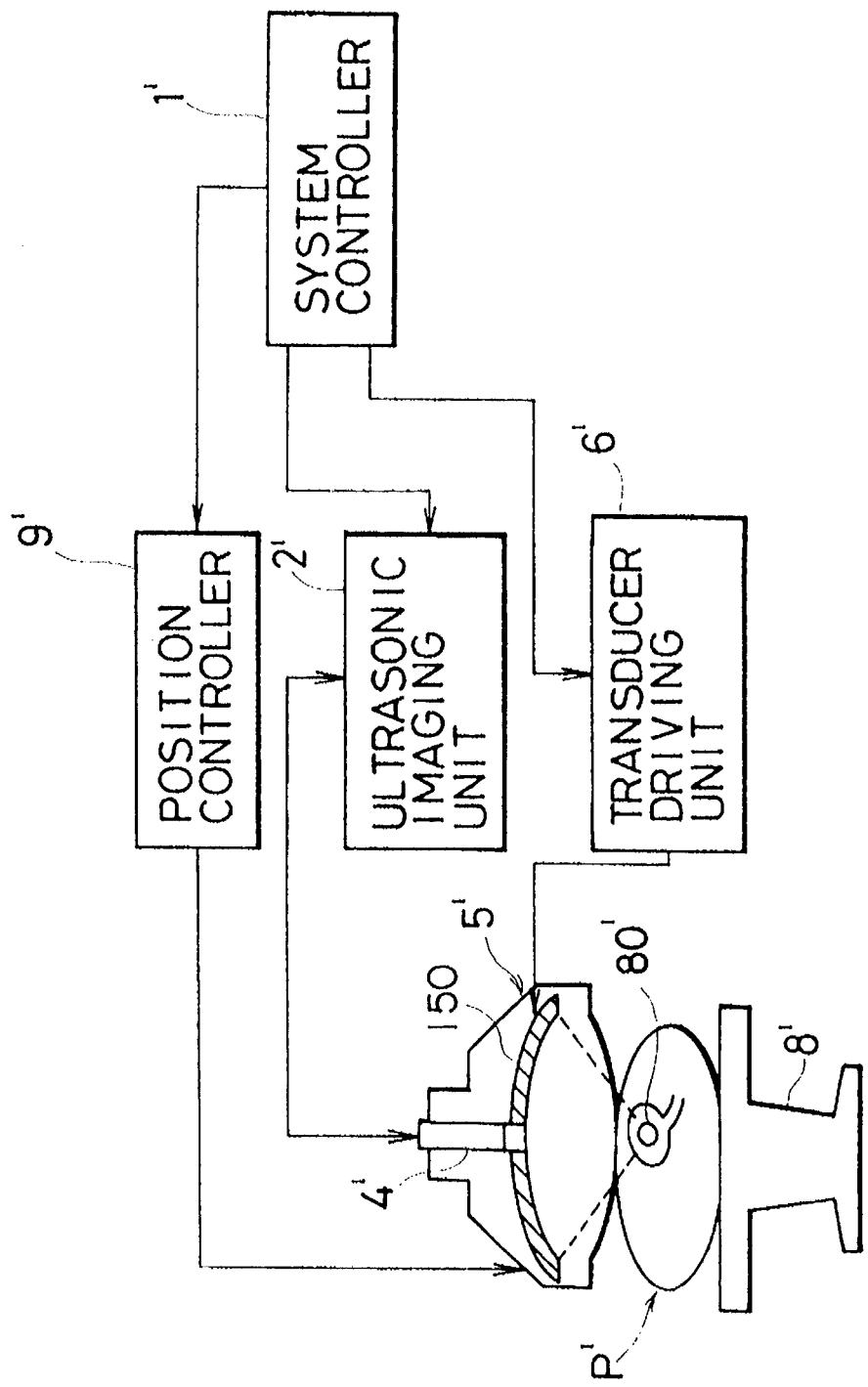
FIG. 20 schematically shows an ultrasonic hyperthermia system.

FIG. 20 shows an ultrasonic hyperthermia system wherein the reference numerals with a "prime" symbol (') correspond to like reference numerals in FIG. 4.

An ultrasonic hyperthermia system comprises an ultrasonic continuous wave generating source 150 having a plurality of ultrasonic continuous wave generating transducer elements; and a transducer driving unit 6' separately driving the plurality of ultrasonic continuous wave generating transducer elements. The ultrasonic continuous wave generating transducer elements are separately driven by controlling delay times to produce a plurality of ultrasonic continuous waves in such a manner that a dimension of a focused region 80' synthesized from a plurality of different focal points formed by the plurality of ultrasonic continuous waves is varied in accordance with a dimension of an object within a biological body P', to be medically cured.

The ultrasonic continuous wave generating transducer elements may be constructed of at least two ring-shaped piezoelectric transducer elements arranged in a concentric form. The ring-shaped piezoelectric transducer elements preferably have substantially the same ultrasonic continuous wave generating surface area.

The ultrasonic hyperthermia system may further comprise a peak temperature controller, rather than the peak pressure controller 13 shown in FIG. 7, controlling drive voltages to vary a peak temperature of the focused region at the medically curing object within the biological body, and an ultrasonic imaging unit 2' ultrasonically scanning a slice portion of the biological body containing the medically curing object to obtain a B-mode ultrasonic image of the slice portion, whereby the medically curing object is displayed in the B-mode ultrasonic image.

The ultrasonic hyperthermia system preferably includes a device, operable in conjunction with the ultrasonic imaging unit 2', for producing a focal-point marker, wherein the focal-point marker is displayed at a focal point of the scanned slice portion of the B-mode ultrasonic image.

The ring-shaped piezoelectric transducer elements may be polygonal ring-shaped piezoelectric transducer elements, each having a concave surface. The ring-shaped piezoelectric transducer elements may be arranged in a substantially flat plane, as viewed in a sectional direction.

MODIFICATION

As apparent from the foregoing description, the present invention is not limited to the above-described preferred embodiments, but may be changed, substituted, and modified without departing from the technical scope and spirit of the invention.

First, for instance, although the drive voltage $V_4$ for the large focused region $SW_4$ is equal to the drive voltage $V_1$ for the small focused region $SW_1$, this drive voltage $V_4$ may be selected to be higher than, or lower than the drive voltage $V_1$.

Various delay times $\tau 1$ to $\tau 6$ may be utilized, for example, 0, 0.4 μS, 0.8 μS, so that the horizontal width of the synthesized focused region becomes approximately 2.36 mm and the peak pressure becomes about 31.05 MPa.

Figure 18A:
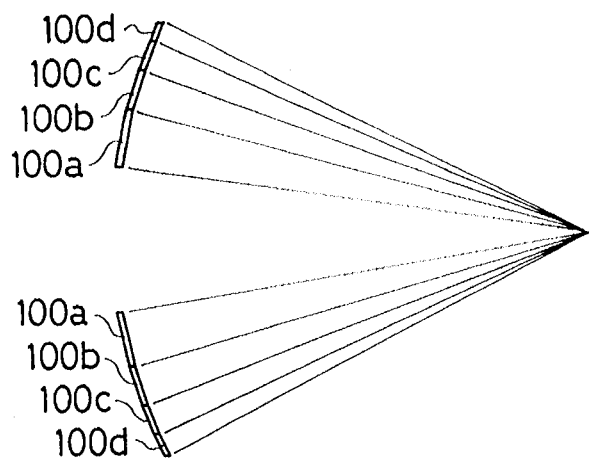
FIGS. 18A, 18b, 19A and 19B schematically illustrate modification of shock-wave generating transducer elements employed in a shock wave generating system of the present invention.
Figure 18B:
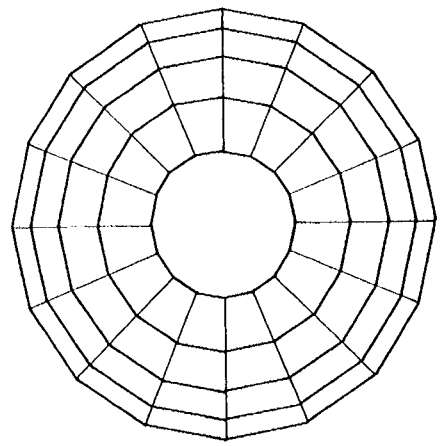

The shape of shock-wave generating transducer element 3 may be varied. For instance, as shown In FIGS. 18A and 18B, polygon type transducer elements "$100a$" to "$100d$" may be employed. Each of these polygon type transducer elements $100a$ to $100d$ is concave. FIG. 18A schematically shows a sectional view of the arrangement of these polygon type transducer elements "$100a$" to "$100d$", taken along the X-direction. FIG. 18A is a top view of this element is arrangement. Alternatively, flat transducer elements (not shown in detail) may be employed instead of the concave transducer elements.

Figure 19A:
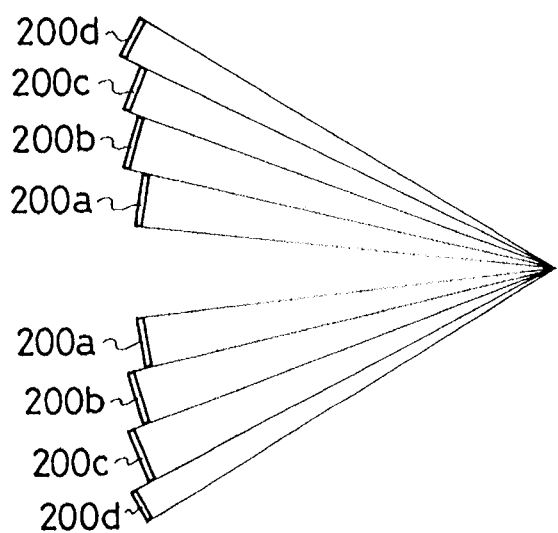
Figure 19B:
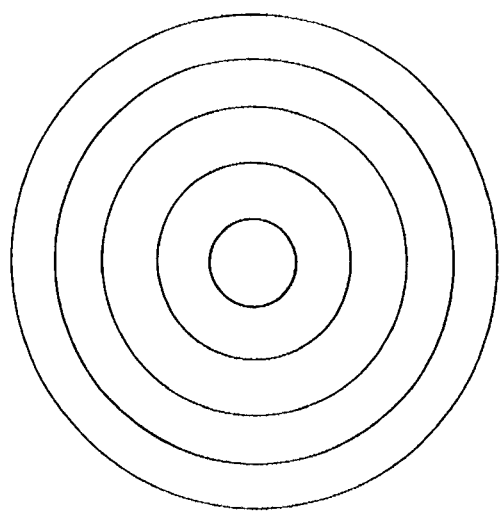

Furthermore, FIG. 19A schematically represents another arrangement of ring-shaped transducer elements "$200a$" to "$200d$" which are arranged in a substantially flat manner, and FIG. 19B schematically shows a top view of this element arrangement.

As previously described in detail, although 6 sets of ring-shaped transducer elements "3a" to "3f" have been employed in the preferred embodiment, the number of transducer elements may be freely selected, but should be greater than, or equal to 2.

The areas of these transducer elements "3a" to "3f" may be made substantially equal to each ocher, or different from each other.

With the shock wave generating apparatus of the present invention, the disintegrating efficiency for the object to be disintegrated, e.g., calculus can be increased, while maintaining medically safe conditions for a patient. Also, hyperthermia curing effects can be increased while maintaining medically safe conditions for a patient in accordance with the continuous wave hyperthermia system of the present invention.

What is claimed is:

1. A shock wave generating system comprising:

a plurality of shock-wave generating elements;

a pulser controller separately driving said plurality of shock-wave generating elements with a common driving voltage;

a delay controller delaying application of said common driving voltage to respective shock-wave generating elements in order to produce a plurality of shock waves which converge at a plurality of different focal points to form a synthesized focused region in accordance with a dimension of a concretion to be disintegrated within a biological body under medical examination;

a drive voltage controller controlling said common driving voltage to vary a peak pressure value in said focused region in accordance with the dimension of the concretion to be disintegrated; and a delay data storage unit storing sets of delay data for use by said pulser controller to control delay times of said plurality of shock-wave generating elements, each set of delay data corresponding to a dimension of a concretion.

2. A shock wave generating system comprising:

shock wave generating means, including a plurality of shock-wave generating elements, for generating a plurality of shock waves;

driving means for separately driving said plurality of shock-wave generating elements by controlling respective delay times to produce a plurality of shock waves which converge at a plurality of different focal points to form a synthesized focused region in accordance with a dimension of a concretion to be disintegrated within a biological body under medical examination;

means for controlling a driving voltage to vary a peak pressure value in said focused region in accordance with a dimension of the concretion to be disintegrated; and means for storing sets of delay data for use by said driving means to control said delay times of said plurality of shock-wave generating elements, each set of delay data corresponding to a dimension of a concretion, wherein said shock-wave generating elements include at least two ring-shaped piezoelectric transducer elements arranged in concentric form.

3. A shock wave generating system as claimed in claim 2, wherein said at least two ring-shaped piezoelectric transducer elements have substantially the same shock-wave generating surface area.

4. A shock wave generating system as claimed in claim 2, further comprising:

ultrasonic imaging means for ultrasonic-scanning a slice portion of said biological body containing said concretion to be disintegrated to obtain a B-mode ultrasonic image of said slice portion, whereby said concretion is displayed in said B-mode ultrasonic image.

5. A shock wave generating system as claimed in claim 4, further comprising:

means, operable in conjunction with said ultrasonic imaging means, for producing a focal-point marker, wherein said focal-point marker is displayed at a focal point of said scanned slice portion of said B-mode ultrasonic image.

6. A shock wave generating system as claimed in claim 2, wherein said ring-shaped piezoelectric transducer elements are polygonal ring-shaped piezoelectric transducer elements, each having a concave surface.

7. A shock wave generating system as claimed in claim 2, wherein said at least two ring-shaped piezoelectric transducer elements are arranged in a substantially flat plane, as viewed in a sectional direction.

8. An ultrasonic hyperthermia system comprising:

ultrasonic continuous wave generating means, including a plurality of ultrasonic continuous wave generating elements, for generating a plurality of ultrasonic continuous waves;

driving means for separately driving said plurality of ultrasonic continuous wave generating elements by controlling respective delay times to produce a plurality of ultrasonic continuous waves which converge at a plurality of different focal points to form a synthesized focused region in accordance with a dimension of an object within a biological body to be medically cured;

means for controlling a driving voltage to vary a peak temperature of said focused region at said object within the biological body; and means for storing sets of delay data for use by said driving means to control said delay times of said plurality of ultrasonic continuous wave generating elements, each set of delay data corresponding to a dimension of an object to be cured;

wherein said ultrasonic continuous wave generating elements include at least two ring-shaped piezoelectric transducer elements arranged in a concentric form.

9. An ultrasonic hyperthermia system as claimed in claim 8, wherein said at least two ring-shaped piezoelectric transducer elements have substantially the same ultrasonic continuous wave generating surface area.

10. An ultrasonic hyperthermia system as claimed in claim 8, further comprising:

ultrasonic imaging means for ultrasonic-scanning a slice portion of said biological body containing said object to obtain a B-mode ultrasonic image of said slice portion, whereby said object is displayed in said B-mode ultrasonic image.

11. An ultrasonic hyperthermia system as claimed in claim 10, further comprising:

means, operable in conjunction with said ultrasonic imaging means, for producing a focal-point marker, wherein said focal-point marker is displayed at a focal point of said scanned slice portion of said B-mode ultrasonic image.

12. An ultrasonic hyperthermia system as claimed in claim 8, wherein said ring-shaped piezoelectric transducer elements are polygonal ring-shaped piezoelectric transducer elements, each having a concave surface.

13. An ultrasonic hyperthermia system as claimed in claim 8, wherein said at least two ring-shaped piezoelectric transducer elements are arranged in a substantially flat plane, as viewed in a sectional direction.

* * * * *